United States Patent
Boyle et al.

[11] Patent Number: 5,913,896
[45] Date of Patent: Jun. 22, 1999

[54] INTERWOVEN DUAL SINUSOIDAL HELIX STENT

[75] Inventors: William J. Boyle, Carlsbad; Rosalinda A. Wong, San Diego; James M. Shy, Chula Vista, all of Calif.

[73] Assignee: Medtronic, Inc., Minneapolis, Minn.

[21] Appl. No.: 08/887,585

[22] Filed: Jul. 3, 1997

Related U.S. Application Data

[63] Continuation of application No. 08/563,715, Nov. 28, 1995, abandoned.

[51] Int. Cl.$^6$ .................... A61F 2/06; A61M 29/00; A61M 29/02
[52] U.S. Cl. .................... 623/1; 623/11; 623/12; 623/901; 606/108; 606/191; 606/192; 606/194; 606/195; 606/198; 128/898
[58] Field of Search ................ 623/1, 11, 12, 623/901; 606/108, 191, 192, 194, 195, 198; 128/898

[56] References Cited

U.S. PATENT DOCUMENTS

| | | | |
|---|---|---|---|
| 4,649,922 | 3/1987 | Wiktor | 128/344 |
| 4,739,762 | 4/1988 | Palmaz | 128/343 |
| 4,856,516 | 8/1989 | Hillstead | 128/343 |
| 4,886,062 | 12/1989 | Wiktor | 128/343 |
| 4,969,458 | 11/1990 | Wiktor | 606/194 |
| 4,994,071 | 2/1991 | MacGregor | 606/194 |
| 5,019,090 | 5/1991 | Pinchuk | 606/194 |
| 5,061,275 | 10/1991 | Wallsten et al. | 623/1 |
| 5,104,404 | 4/1992 | Wolff | 623/1 |
| 5,116,365 | 5/1992 | Hillstead | 623/1 |
| 5,133,732 | 7/1992 | Wiktor | 606/195 |
| 5,161,547 | 11/1992 | Tower | 128/898 |
| 5,282,823 | 2/1994 | Schwartz et al. | 606/198 |
| 5,342,348 | 8/1994 | Kaplan | 604/891.1 |
| 5,354,308 | 10/1994 | Simon et al. | 606/198 |
| 5,366,504 | 11/1994 | Andersen et al. | 623/11 |
| 5,370,683 | 12/1994 | Fontaine | 623/1 |
| 5,382,261 | 1/1995 | Palmaz | 606/158 |
| 5,389,106 | 2/1995 | Tower | 606/198 |
| 5,405,377 | 4/1995 | Cragg | 623/1 |
| 5,443,498 | 8/1995 | Fontaine | 623/1 |
| 5,503,636 | 4/1996 | Schmitt et al. | 606/200 |
| 5,507,767 | 4/1996 | Maeda et al. | 606/198 |
| 5,549,663 | 8/1996 | Cottone, Jr. | 623/1 |
| 5,613,981 | 3/1997 | Boyle et al. | 606/198 |

FOREIGN PATENT DOCUMENTS

| | | |
|---|---|---|
| 0645125 | 3/1995 | European Pat. Off. |
| 9412136 | 6/1994 | WIPO |
| 9529646 | 9/1995 | WIPO ............... A61F 2/04 |

OTHER PUBLICATIONS

Application for United States Letters Patent for "Bidirectional Dual Sinusoidal Helix Stent", William J. Boyle, et al., Serial No. 08/426,310, Filing Date: Apr. 21, 1995.

*Primary Examiner*—Paul B. Prebilic
*Assistant Examiner*—Choon P. Koh
*Attorney, Agent, or Firm*—Dianne Plunkett Latham; Harold R. Patton

[57] ABSTRACT

A method and apparatus for a radially expandable stent for implantation within a body vessel, comprising a first and second wire having a series of alternating peaks and valleys. The valleys of the first wire are braided with the peaks of the second wire forming a braided region with the interwoven first and second wire being wound into a continuous helix having a hollow cylindrical shape. The peaks of the first wire of the continuous helix may be welded to the adjacent valleys of the second wire of the continuous helix. The peaks and valleys of the first wire may symmetrically intersect with the peaks and valleys of the second wire to form a uniform series of crossings thereby permitting even expansion of the first and second wires. The proximal end of the first wire may be attached to the proximal end of the second wire. The distal end of the first wire may be attached to the distal end of the second wire. A means within the interwoven first and second wires of the continuous helix may be included for expansion thereof.

27 Claims, 3 Drawing Sheets

INTERWOVEN DUAL SINUSOIDAL HELIX STENT

This application is a continuation of application Ser. No. 08/563,715 filed on Nov. 28, 1995, now abandoned.

FIELD OF THE INVENTION

The present invention relates to intravascular stent implants for maintaining vascular patency in humans and animals and more particularly to a stent in the form of an interwoven dual sinusoidal helix stent.

BACKGROUND OF THE INVENTION

Percutaneous transluminal coronary angioplasty (PTCA) is used to reduce arterial build-up of cholesterol fats or atherosclerotic plaque. Typically a guidewire is steered through the vascular system to the site of therapy. A guiding catheter, for example, can then be advanced over the guidewire and a balloon catheter advanced within the guiding catheter over the guidewire. The balloon at the distal end of the catheter is inflated causing the site of the stenosis to widen. The dilatation of the occlusion, however, can form flaps, fissures and dissections which threaten re-closure of the dilated vessel or even perforations in the vessel wall. Implantation of a metal stent can provide support for such flaps and dissections and thereby prevent reclosure of the vessel or provide a patch repair for a perforated vessel wall until corrective surgery can be performed. Reducing the possibility of restenosis after angioplasty reduces the likelihood that a secondary angioplasty procedure or a surgical bypass operation will be necessary.

An implanted prosthesis such as a stent can preclude additional procedures and maintain vascular patency by mechanically supporting dilated vessels to prevent vessel collapse. Stents can also be used to repair aneurysms, to support artificial vessels as liners of vessels or to repair dissections. Stents are suited to the treatment of any body lumen, including the vas deferens, ducts of the gallbladder, prostate gland, trachea, bronchus and liver. The body lumens range in size from 3.0 mm in the coronary vessels to 28 mm in the aortic vessel. The invention applies to acute and chronic closure or reclosure of body lumens.

A stent is a cylindrically shaped wire formed device intended to act as a permanent prosthesis. A stent is deployed in a body lumen from a radially compressed configuration into a radially expanded configuration which allows it to contact and support a body lumen. The stent can be made to be radially self-expanding or expandable by the use of an expansion device. The self expanding stent is made from a resilient springy material while the device expandable stent is made from a material which is plastically deformable. A plastically deformable stent can be implanted during a single angioplasty procedure by using a balloon catheter bearing a stent which has been crimped onto the balloon. Stents radially expand as the balloon is inflated, forcing the stent into contact with the body lumen thereby forming a supporting relationship with the vessel walls. Deployment is effected after the stent has been introduced percutaneously, transported transluminally and positioned at a desired location by means of the balloon catheter.

Various shapes of stents are known in the art. U.S. Pat. No. 4,649,922 to Wiktor for "Catheter Arrangement Having A Variable Diameter Tip and Spring Prothesis" discloses a linearly expandable spring-like stent. U.S. Pat. No. 4,886,062 to Wiktor for "Intravascular Radially Expandable Stent and Method of Implant" discloses a two-dimensional zig-zag form, typically a sinusoidal form. U.S. Pat. No. 4,969,458 to Wiktor for "Intracoronary Stent and Method of Simultaneous Angioplasty and Stent Implant" discloses a stent wire coiled into a limited number of turns wound in one direction then reversed and wound in the opposite direction with the same number of turns, then reversed again and so on until a desired length is obtained. U.S. Pat. No. 5,133,732 to Wiktor for "Intravascular Stent" discloses a stent body coiled from a generally continuous wire with a deformable zig-zag structure with a means for preventing the stent body from stretching along its longitudinal axis.

U.S. Pat. No. 5,019,090 to Pinchuk for "Radially Expandable Endoprosthesis and the Like" discloses a plurality of adjacent generally circumferential sections that are substantially axially positioned with respect to each other. At least one of the generally circumferential sections has a generally circumferentially disposed expandable segment that imparts circumferential and radial expandability to the stent.

U.S. Pat. No. 5,104,404 to Wolff for "Articulated Stent" discloses a stent made up of a number of wires welded together and then connected together with hinges to provide articulation.

U.S. Pat. No. 5,116,365 to Hilistead for a "Stent Apparatus and Method for Making" discloses a stent constructed from two elongated wires which are each bent into a series of tight bends. The two wires are permanently adhered at a first interconnection junction. The two wires are then wrapped around a mandrel repeatedly forming two opposing series of interconnections.

U.S. Pat. No. 5,161,547 to Tower for a "Method of Forming an Intravascular Radially Expandable Stent" discloses a stent formed from a fine wire bent into a serpentine flat ribbon which is wound around a mandrel into a cylindrical sleeve and welded to a pigtail of the wire.

U.S. Pat. No. 5,342,348 to Kaplan for a "Method and Device for Treating and Enlarging Body Lumens" discloses a delivery matrices which provide for the controlled release of bioactive substances. The tubular structure includes a perforated cylinder and a filament is interwoven through the perforations in the cylinder.

U.S. Pat. No. 5,354,308 to Simon for a "Metal Wire Stent" discloses a frame adapted to assume a first condition in which the frame is relatively rigid and substantially tubular in configuration and a second condition in which the frame is flexible, of reduced stress, and collapsible, such that the second condition walls of the frame are adapted to be positioned against each other to form a stent diameter substantially equal to the combined thickness of the frame walls in abutting engagement with each other, the frame in its second condition being substantially devoid of bias therein urging the frame to assume the first configuration. The tubular body mesh may be formed of polygonal or hexagonal cells.

U.S. Pat. No. 5,443,498 to Fontaine for "Vascular Stent and Method of Making and Implanting a Vascular Stent" discloses a continuous wire which is formed into a substantially tubular body having a plurality of oblong, open cells which are staggered around the circumference of the tube. When the body is formed in its unexpanded state, the long sides of each oblong cell are arranged substantially parallel to the longitudinal axis of the tubular body. Adjoining cells may then be bonded together at a point between adjacent parallel sides on a cell. When the body is expanded, the adjacent sides of each cell extend oblique to the longitudinal axis of the body.

Co-pending patent U.S. Ser. No. 08/426,310 to Boyle et al. for "Bidirectional Dual Sinusoidal Helix Stent" discloses a first sinusoidal wave form wrapped around a mandrel such that the sinusoidal helix wraps form an acute angle with respect to the forming mandrel. The second sinusoidal wave form is wrapped around a mandrel such that the sinusoidal helix wraps form an obtuse angle with respect to the forming mandrel. The two sinusoidal helix wave forms are connected only at the two ends of the stent. The waveforms are not interconnected along the length of the stent.

WO 94/12136 to Anderson et al. for "Stent for Body Lumen Exhibiting Peristaltic" discloses knitting preferably a nitinol wire into a pattern of overlapping loops selected such that from a relaxed state each row of loops may shift axially relative to and independently of the rows on either side.

SUMMARY OF THE INVENTION

It is an object of the invention to provide a wire-wound stent having good wire coverage and hoop strength as well as to reduce longitudinal slippage during stent expansion, prevent wire overlap during stent expansion, provide longitudinal support during expansion, reduce stent profile and reduce the likelihood of thrombus formation.

The present invention is accomplished by providing a method and apparatus for a radially expandable stent for implantation within a body vessel, comprising a first and second wire having a series of alternating peaks and valleys. The valleys of the first wire are braided with the peaks of the second wire forming a braided region with the interwoven first and second wire being wound into a continuous helix having a hollow cylindrical shape. The peaks of the first wire of the continuous helix may be welded to the adjacent valleys of the second wire of the continuous helix. The peaks and valleys of the first wire may symmetrically intersect with the peaks and valleys of the second wire to form a uniform series of crossings thereby permitting even expansion of the first and second wires. The proximal end of the first wire may be attached to the proximal end of the second wire. The distal end of the first wire may be attached to the distal end of the second wire. A means within the interwoven first and second wire continuous helix may be included for expansion thereof.

DETAILED DESCRIPTION OF THE PREFERRED EMBODIMENTS

Figure 1:
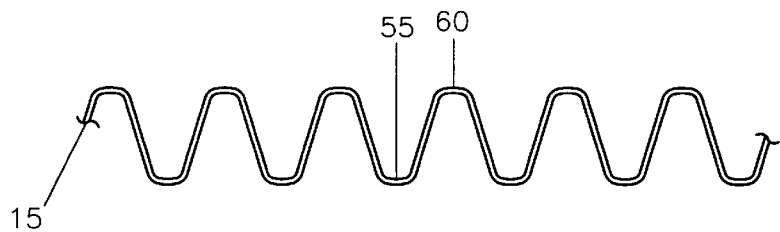
FIG. 1 is a side elevation view of a first wire segment (or a second wire segment) sinusoidal wave form.
Figure 3:
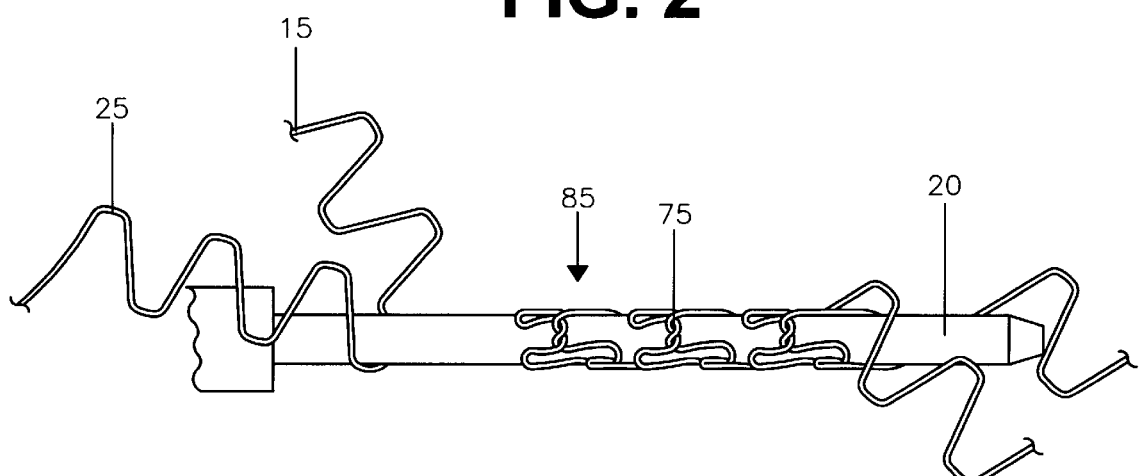
FIG. 3 is a side elevation view of the braided segment according to FIG. 2 being wrapped into a continuous helix onto the forming mandrel.

Referring to FIG. 1, a first wire segment 15 is formed into a sinusoidal wave form helix pattern the length of the stent by a means such as passing the wire through gears such as disclosed in U.S. Pat. No. 2,153,936 issued to Owens et al. A second wire segment 25 is similarly formed into a preformed sinusoidal wave form helix pattern the length of the stent 10 by a means such as passing the wire through gears. The first wire segment 15 is braided around a second wire segment 25 forming braided region 75. Both ends of wires 15 and 25 are left unbraided. The braided first and second wire segments 15 and 25 are wound at an angle around a forming mandrel 20 as in FIG. 3. The outer diameter of the mandrel 20 can range from 0.175 inches to 0.065 inches depending on the balloon 35 size to be used and most preferably a 0.100 inch outer diameter mandrel 20 which is suitable for the most common balloon 35 sizes.

The preferred form of the sinusoidal wave of the first wire segment 15 and the second wire segment would have a length of 0.150 inches to 0.090 inches and a wave amplitude of between 0.080 inches and 0.050 inches. Any wave length and amplitude combination that would provide adequate vessel 50 hoop strength and vessel 50 coverage is appropriate. The stent 10 must expand evenly and permit the balloon 35 to expand evenly. The stent 10 of this invention and balloon 35 can be transported via a standard #8 French guiding catheter. Once on location, the stent 10 can be expanded radially by the expansion of the balloon 35; a ratio of 2.75:1 can be achieved with a wire diameter of 0.005 inches and an initial stent diameter of 0.060 inches.

Figure 2:
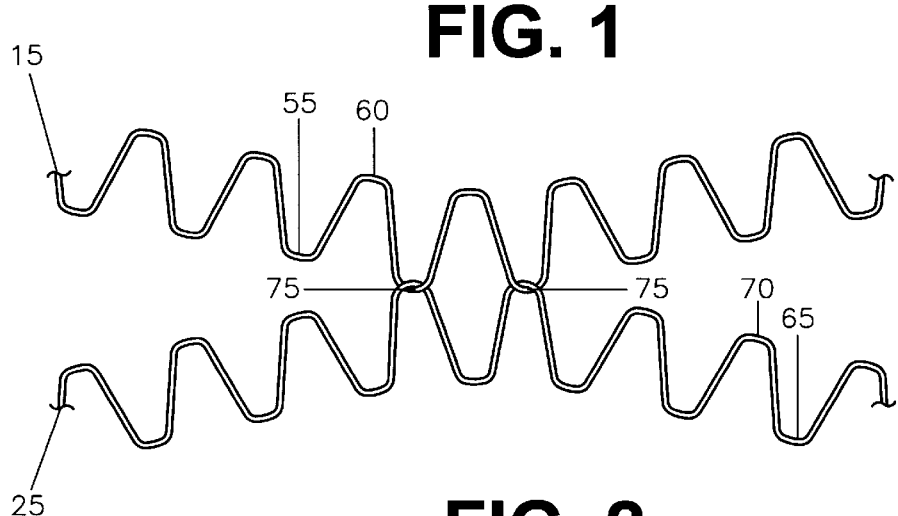
FIG. 2 is a side elevation view of a preferred embodiment of a first and second wire segment braided according to this invention.

The first wire segment 15 has a series of alternating valleys 55 and peaks 60 which form the helix. Similarly, the second wire segment 25 has a series of alternating valleys 65 and peaks 70 which form the helix. The first wire segment 15 and the second wire segment 25 are aligned in a longitudinal direction. The valleys 55 of the first wire segment 15 are braided 75 with the peaks 70 of the second wire segment 25 as shown in FIG. 2. The resulting braided geometry forms a single dual sinusoidal waveform structure with the ends unbraided. The interwoven first wire segment 15 and second wire segment 25 are then wrapped at an angle around a forming mandrel 20 as in FIG. 3 to form a continuous helix 85.

After the braided regions 75 are formed, the braided regions 75, or the entire structure, can be flattened to reduce the profile or wall thickness of the stent. This can be accomplished by placing the stent over a round mandrel and compressing it against the mandrel by a variety of mechanical means or by a hydraulic forming press. The flattened braided profile would then be thinner than that of unflattened, overlapping segments. Braiding and flattening also reduces the longitudinal sliding between the two sinusoidal wave forms and wire overlap during stent expansion.

Figure 4:
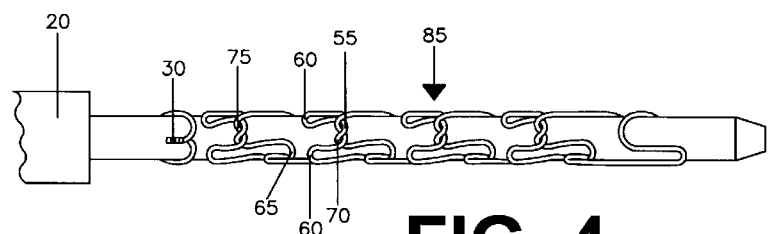
FIG. 4 is a side elevation view showing an overall view of a stent prosthesis fitted over a mandrel with connected first and second wire segments.
Figure 5:
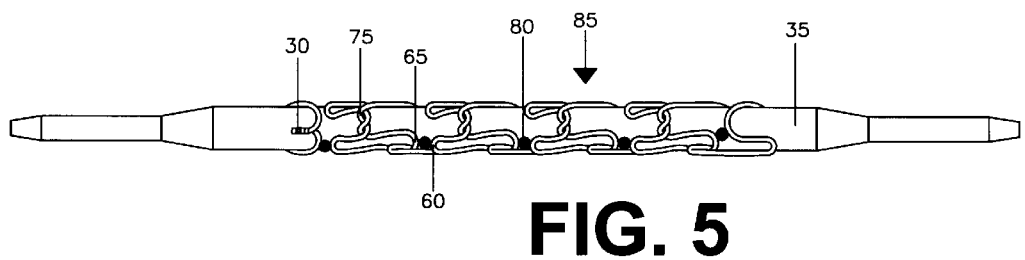
FIG. 5 is a side elevation view showing an overall view of a stent prosthesis fitted over a balloon with connected first and second wire segments as well as welds.

Adjacent helix peaks could optionally be welded. As the interwoven first wire segment 15 and second wire segment 25 are wrapped at an angle around a forming mandrel 10 to form a continuous helix 85, peaks 60 of the first wire segment and valleys 65 of the second wire segment will fall adjacent to each other. FIG. 4 shows a stent before welding. FIG. 5 shows a stent with welds 80 included. Although the FIG. 5 welds 80 are shown to align longitudinally, this is not always necessary or desirable. In some cases it may be desirable to make only selective welds 80 around the circumference of the stent in order to prevent the stent from shortening excessively as it expands.

Welding adjacent helix peaks 60 and valleys 65 precludes longitudinal slippage. The additional longitudinal support provided by welding the adjacent helix peaks 60 and valleys 65 prevents wire overlap during stent expansion. The increased stabilization resulting from the welding of peaks 60 and valleys 65 also facilitates reaching lesions which are distal to the stented lesion. This is required in the circumstance when a stent is deployed and a subsequent lesion distal to the stented lesion must be treated. A balloon catheter bearing a second stent can then be passed through the stent which was first deployed with less risk of the second stent catching and deforming the first stent.

A forming mandrel sequence can provide a gradual reduction in the stent 10 outer diameter by the use of applied finger pressure under microscopic observation. Although it is possible to go directly from a 0.150 inch stent outer diameter to a 0.065 inch stent outer diameter by placing stent 10 directly onto the balloon 35 from the forming mandrel and make an acceptable stent, it is more difficult to maintain proper alignment of the stent wires by doing so. Thus it is preferred that the stent 10 is further processed from a 0.150 inch diameter forming mandrel by pressing it onto a 0.100 inch diameter forming mandrel, thereafter pressing it onto a 0.080 inch diameter forming mandrel and finally pressing it onto a 0.065 inch diameter forming mandrel before being applied to the balloon 35. Those skilled in the art would recognize that a variety of acceptable mandrel sizes could be used in the forming sequence.

After the braided stent 10 has been reduced to the objective outer diameter, the proximal end of the first wire segment 15 and the proximal end of the second wire segment 25 are attached to each other. The distal end of the first wire segment 15 and the distal end of the second wire segment 25 are then attached to each other. The means of attachment may include looping the end segments together, twisting 30 (as seen in FIG. 4), biocompatible adhesive, brazing, welding or stamping.

Figure 6:
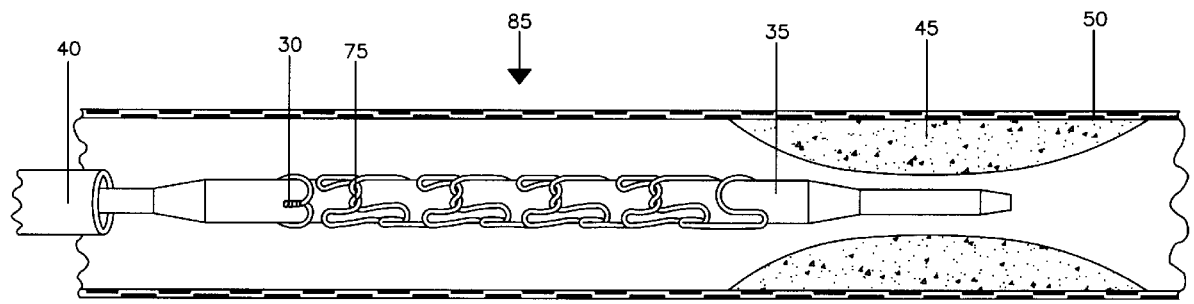
FIG. 6 is the balloon and stent assembly advanced within a vessel, entering a partial occlusion.
Figure 7:
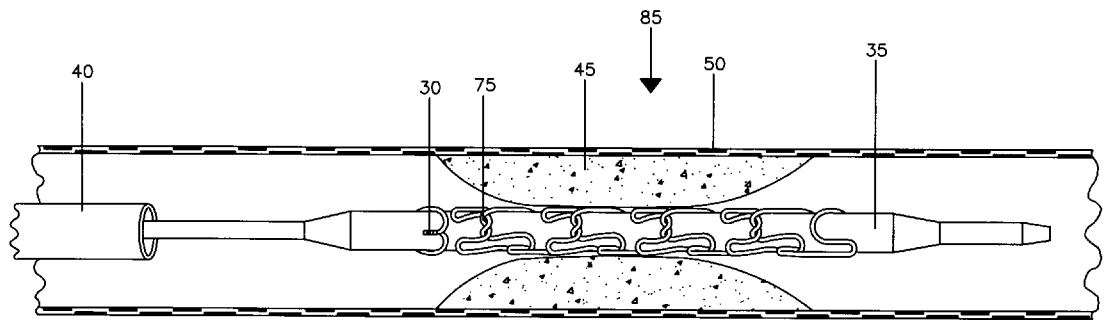
FIG. 7 is similar to FIG. 6 showing the balloon and stent assembly inside a partially occluded vessel.
Figure 8:
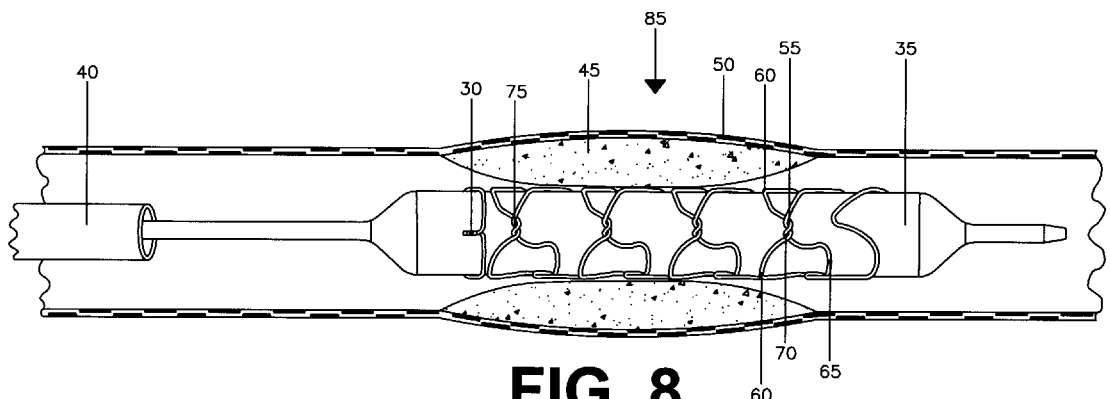
FIG. 8 is similar to FIG. 7 with the balloon inflated and the stent radially expanded illustrating an angioplasty procedure with a simultaneous deployment and implantation of a permanent prosthesis stent.
Figure 9:
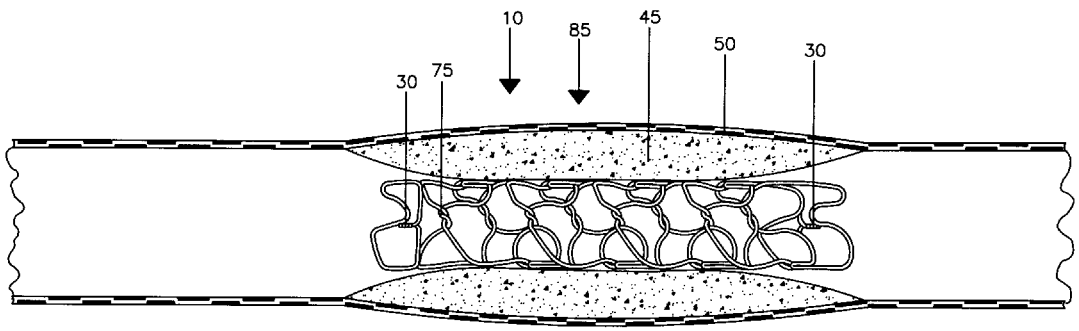
FIG. 9 is a view similar to FIG. 8 showing the plaque compressed and the prosthesis stent implanted and retained after removal of the balloon.

The stent 10 is removed from the mandrel and placed over a suitable expandable diameter device such as an inflatable balloon 35 which is typically used for angioplasty procedures as seen in FIG. 5. A stent can be implanted during a single angioplasty procedure by using a balloon catheter bearing a stent 10 which has been preferably crimped with a suitable crimping tool onto the balloon 35 as shown in FIG. 5. Manually squeezing the stent 10 over the balloon 35 is also acceptable. FIG. 6 shows how the balloon 35 and stent 10 assembly emanate from a guiding catheter 40 inside vessel 50 and are advanced toward a partial occlusion 45. Once the balloon 35 is lodged in the stenosis 45 as seen in FIG. 7, the balloon 35 can be inflated as in FIG. 8 using standard angioplasty procedures and techniques. The stent 10 is thereby radially expanded as the balloon 35 is inflated, causing the stent 10 to contact the body lumen thereby forming a supporting relationship with the vessel walls as seen in FIG. 9. As balloon 35 expands, so does stent 10. The expanding balloon 35 together with the stent 10 compresses the plaque 45 in the stenosis and prevents possible reocclusion. When the angioplasty procedure is completed, balloon 35 is deflated and withdrawn leaving stent 10 fly implanted within vessel 50. Previously occluded vessel 50 is recanalized and patency is restored. FIG. 9 shows stent 10 firmly implanted and imbedded in compressed plaque 45, providing both adequate support as well as a smooth lumen void of protrusions. Any protrusions are conducive to turbulent blood flow and potential formation of thrombosis.

The stent wire 15, 25 can have a diameter of 0.001 inches to 0.015 inches. A typical stent 10 ranges from 5 mm to 50 mm in length. The balloon expandable stent 10 can be made of an inert, biocompatible material with high corrosion resistance that can be plastically deformed at low-moderate stress levels such as tantalum, the preferred embodiment. Other acceptable materials include nickel titanium, stainless steel, titanium ASTM F63-83 Grade 1, niobium or high carat gold K 19-22. A self-expanding device can be made by the use of superelastic NiTi such as nitinol manufactured by Raychem or Forukawa.

A problem with solid tantalum stents is that they may glow too brightly under fluoroscopy making it difficult to see the stent edges. One solution is to use clad materials. Clad materials are composed of one metal on the outside and another metal on the inside. With this design, a radiopaque material such as tantalum could be used on the inside. A higher strength material, such as stainless steel or a superalloy such as MP-35N, could be used on the outside thereby reducing the brightness of the tantalum. Applicant tested using three 0.005 inch wire diameter stent samples. The first sample comprised a tantalum control sample with more than 99.7 weight % tantalum. The second sample comprised a stainless steel 316 clad alloy with 25% tantalum by volume. The third sample comprised an MP-35N clad alloy with 33% tantalum by volume. Each of the three wire samples were wrapped around a plastic test tube approximately ½ inches in diameter. An 80 KV heart grid simulating the density of a human thorax was placed between the fluoroscopy energy source and the wire samples. The third sample proved the most suitable given that the first sample was too bright with less well defined edges and the second sample was somewhat dim.

As shown in FIG. 5, stent 10 is centrally located and positioned with respect to the length of balloon 35. The stent 10 turns are evenly spaced so that when the stent 10 is expanded as shown in FIG. 8, the stent 10 will provide even support inside vessel 50, and resist external loading.

The preceding specific embodiments are illustrative of the practice of the invention. It is to be understood, however, that other expedients known to those skilled in the art or disclosed herein, may be employed without departing from the spirit of the invention or the scope of the appended claims.

No. Component

10 Stent
15 First Wire Segment
20 Mandrel
25 Second Wire Segment
30 Twist
35 Balloon
40 Guide Catheter
45 Plaque
50 Vessel
55 Valley First Wire Segment
60 Peak First Wire Segment
65 Valley Second Wire Segment
70 Peak Second Wire Segment
75 Braided Region
80 Weld
85 Continuous Helix

What is claimed is:

1. A radially expandable stent for implantation within a body vessel, comprising:

a first wire having a preformed series of peaks alternating with valleys therein, each peak and valley being connected by a substantially straight segment, the first wire having a proximal end and a distal end;

a second wire having a preformed series of peaks alternating with valleys therein each peak and valley being connected by a substantially straight segment, the second wire having a proximal end and a distal end;

the first wire being interwoven with the second wire such that each valley of the first wire is interwoven with one respective peak of the second wire with each interweaving forming a braid, the braid having a first outer diameter, the first outer diameter of one or more braids are flattened using a means whereby a wall thickness of the braid is reduced resulting in a second outer diameter of the braid which is less than the first outer diameter; and the interwoven first and second wires being wound into a continuous helix having a hollow cylindrical shape.

2. The stent according to claim 1 wherein the first and second wires are formed of a biocompatible metal that can be plastically deformed at low to moderate stress levels.

3. The stent according to claim 1 wherein the first and second wires are formed of a biocompatible clad metal having a radiopaque material covered with a higher strength material.

4. The stent according to claim 1 wherein the first and second wires are formed of MP-35N with at least 33% tantalum by volume.

5. The stent according to claim 1 wherein the first and second wires are formed of a stainless steel alloy 316 with greater than 25% tantalum by volume.

6. The stent according to claim 1 having a means within the interwoven first and second wires of the continuous helix for expanding the interwoven first and second wires of the continuous helix.

7. The stent according to claim 1 wherein at least one peak of the first or second wire of the continuous helix is welded to an adjacent valley of the first or second wire of the continuous helix.

8. The stent according to claim 1 wherein the first and second wires are formed of a biocompatible clad metal having a radiopaque material covered with a higher strength material.

9. A radially expandable stent for implantation within a body vessel, comprising:

a first wire having a preformed series of peaks alternating with valleys therein, each peak and valley being connected by a substantially straight segment, the first wire having a proximal end and a distal end;

a second wire having a preformed series of peaks alternating with valleys therein, each peak and valley being connected by a substantially straight segment, the second wire having a proximal end and a distal end;

the first wire being interwoven with the second wire such that each valley of the first wire is interwoven with one respective peak of the second wire with each interweaving forming a braid, the braid having a first outer diameter, the first outer diameter of one or more braids are flattened using a means whereby a wall thickness of the braid is reduced resulting in a second outer diameter of the braid which is less than the first outer diameter;

the interwoven first and second wires being wound into a continuous helix having a hollow cylindrical shape; and the peaks and valleys of the first wire symmetrically intersecting with the peaks and valleys of the second wire to form a uniform series of crossings thereby permitting even expansion of the first and second wires.

10. The stent according to claim 9 wherein the first and second wires are formed of a biocompatible metal that can be plastically deformed at low to moderate stress levels.

11. The stent according to claim 9 wherein the first and second wires are formed of a biocompatible clad metal having a radiopaque material covered with a higher strength material.

12. The stent according to claim 9 wherein the first and second wires are formed of MP-35N with at least 33% tantalum by volume.

13. The stent according to claim 9 wherein the first and second wires are formed of a stainless steel alloy 316 with greater than 25% tantalum by volume.

14. The stent according to claim 9 having a means for expanding the first and second wires.

15. The stent according to claim 9 wherein at least one peak of the first or second wire of the continuous helix is welded to an adjacent peak of the first or second wire of the continuous helix.

16. The stent according to claim 9 wherein the first and second wires are formed of a biocompatible clad alloy having a radiopaque material covered with a higher strength material.

17. A radially expandable stent for implantation within a body vessel, comprising:

a first wire having a preformed series of peaks alternating with valleys therein, each peak and valley being connected by a substantially straight segment, the first wire having a proximal end and a distal end;

a second wire having a preformed series of peaks alternating with valleys therein, each peak and valley being connected by a substantially straight segment, the second wire having a proximal end and a distal end;

the first wire being interwoven with the second wire such that each valley of the first wire is interwoven with one respective peak of the second wire with each interweaving forming a braid, the braid having a first outer diameter, the first outer diameter of one or more braids are flattened using a means whereby a wall thickness of the braid is reduced resulting in a second outer diameter of the braid which is less than the first outer diameter;

the interwoven first and second wires being wound into a continuous helix having a hollow cylindrical shape; and the proximal end of the first wire being attached to the proximal end of the second wire, and the distal end of the first wire being attached to the distal end of the second wire.

18. A method for making a stent body for implantation within a body vessel comprising:

preforming a first wire into a sinusoidal wave pattern having a series of peaks alternating with valleys, each peak and valley being connected by a substantially straight segment, the first wire having a proximal end and a distal end;

preform a second wire into a sinusoidal wave pattern having a series of peaks alternating with valleys, each peak and valley being connected by a substantially straight segment, the second wire having a proximal end and a distal end;

interweaving the first wire with the second wire such that each valley of the first wire is braided with one respective peak of the second wire with each interweaving forming a braid, the braid having a first outer diameter, the first outer diameter of one or more braids are flattened using a means whereby a wall thickness of the braid is reduced resulting in a second outer diameter of the braid which is less than the first outer diameter; and winding the interwoven first and second wires on a cylindrical mandrel into a continuous helix having a cylindrical shape such that the alternating peaks and valleys are retained.

19. The method of claim 18 comprising a further step of attaching the proximal end of the first wire to the proximal end of the second wire; and attaching the distal end of the first wire to the distal end of the second wire.

20. The method of claim 18 comprising a further step of interweaving the first wire with the second wire such that the peaks and valleys of the first wire symmetrically intersect with the peaks and valleys of the second wire to form a uniform series of crossings thereby permitting even expansion of the first and second wires.

21. The method of claim 18 including a further step of welding at least one peak of the first or second wire of the continuous helix to an adjacent valley of the first or second wire of the continuous helix.

22. The method of claim 18 including a further step of having a means within the interwoven first and second wires of the continuous helix for expanding the interwoven first and second wires of the continuous helix.

23. The method of claim 18 including a further step of flattening the first outer diameter of one or more braids using a means whereby a wall thickness of the braid is reduced resulting in a second outer diameter of the braid which is less than the first outer diameter.

24. A radially expandable stent for implantation within a body vessel, comprising:

a first wire having a preformed series of peaks alternating with valleys therein, each peak and valley being connected by a substantially straight segment, the first wire having a proximal end and a distal end;

a second wire having a preformed series of peaks alternating with valleys therein, each peak and valley being connected by a substantially straight segment, the second wire having a proximal end and a distal end;

the first wire being interwoven with the second wire such that at least a pair of immediately adjacent peaks of the first wire are interwoven with at least a pair of respective counterpart immediately adjacent valleys of the second wire with each interweaving forming a braid, the braid having a first outer diameter, the first outer diameter of one or more braids are flattened using a means whereby a wall thickness of the braid is reduced resulting in a second outer diameter of the braid which is less than the first outer diameter; and the interwoven first and second wires being wound into a continuous helix having a hollow cylindrical shape.

25. A radially expandable stent for implantation within a body vessel, comprising:

a first wire having a preformed series of peaks alternating with valleys therein, each peak and valley being connected by a substantially straight segment, the first wire having a proximal end and a distal end;

a second wire having a preformed series of peaks alternating with valleys therein, each peak and valley being connected by a substantially straight segment, the second wire having a proximal end and a distal end;

the first wire being interwoven with the second wire such that at least a pair of immediately adjacent peaks of the first wire are interwoven with at least a pair of respective counterpart immediately adjacent valleys of the second wire with each interweaving forming a braid, the braid having a first outer diameter, the first outer diameter of one or more braids are flattened using a means whereby a wall thickness of the braid is reduced resulting in a second outer diameter of the braid which is less than the first outer diameter;

the interwoven first and second wires being wound into a continuous helix having a hollow cylindrical shape; and the peaks and valleys of the first wire symmetrically intersecting with the peaks and valleys of the second wire to form a uniform series of crossings thereby permitting even expansion of the first and second wires.

26. A radially expandable stent for implantation within a body vessel, comprising:

a first wire having a preformed series of peaks alternating with valleys therein, each peak and valley being connected by a substantially straight segment, the first wire having a proximal end and a distal end;

a second wire having a preformed series of peaks alternating with valleys therein, each peak and valley being connected by a substantially straight segment, the second wire having a proximal end and a distal end;

the first wire being interwoven with the second wire such that at least a pair of immediately adjacent peaks of the first wire are interwoven with at least a pair of respective counterpart immediately adjacent valleys of the second wire with each interweaving forming a braid, the braid having a first outer diameter, the first outer diameter of one or more braids are flattened using a means whereby a wall thickness of the braid is reduced resulting in a second outer diameter of the braid which is less than the first outer diameter;

the interwoven first and second wires being wound into a continuous helix having a hollow cylindrical shape; and the proximal end of the first wire being attached to the proximal end of the second wire, and the distal end of the first wire being attached to the distal end of the second wire.

27. A method for making a stent body for implantation within a body vessel comprising:

preforming a first wire into a sinusoidal wave pattern having a series of peaks alternating with valleys, each peak and valley being connected by a substantially straight segment, the first wire having a proximal end and a distal end;

preforming a second wire into a sinusoidal wave pattern having a series of peaks alternating with valleys, each peak and valley being connected by a substantially straight segment, the second wire having a proximal end and a distal end;

interweaving the first wire with the second wire such that at least a pair of immediately adjacent peaks of the first wire are braided with at least a pair of respective immediately adjacent valleys of the second wire with each interweaving forming a braid, the braid having a first outer diameter, the first outer diameter of one or more braids are flattened using a means whereby a wall thickness of the braid is reduced resulting in a second outer diameter of the braid which is less than the first outer diameter; and winding the interwoven first and second wires on a cylindrical mandrel into a continuous helix having a cylindrical shape such that the alternating peaks and valleys are retained.

* * * * *